US006261573B1

(12) United States Patent
Loebelenz et al.

(10) Patent No.: US 6,261,573 B1
(45) Date of Patent: Jul. 17, 2001

(54) IMMUNOADJUVANTS

(75) Inventors: Jean R. Loebelenz, Essex; Bryan E. Roberts, Cambridge; Alexander K. Andrainov, Belmont, all of MA (US); Sharon A. Jenkins, Bethlehem, NH (US)

(73) Assignee: Avant Immunotherapeutics, Inc., Needham, MA (US)

( * ) Notice: Subject to any disclaimer, the term of this patent is extended or adjusted under 35 U.S.C. 154(b) by 0 days.

(21) Appl. No.: 09/426,361

(22) Filed: Oct. 25, 1999

Related U.S. Application Data

(60) Provisional application No. 60/106,326, filed on Oct. 30, 1998.

(51) Int. Cl.[7] .......................... A61K 45/00; A61K 51/00
(52) U.S. Cl. ...................... 424/278.1; 424/1.11; 435/5; 514/110; 514/75; 514/137
(58) Field of Search ............................... 424/183.1, 278.1, 424/290.1, 1.11; 435/5; 514/110, 75, 137

(56) References Cited

U.S. PATENT DOCUMENTS 5,102,663 * 4/1992 Livingston et al. .................. 424/88

OTHER PUBLICATIONS

Powell et al. Vaccine Design: The Subunit and Adjuvnat Approach. Plenum Press, New York: Ulrich and Myers. 1995, pp. 495–524.*

Payne et al. Vaccine, 1998, vol. 16, No. 1, pp. 92–98.*

* cited by examiner

*Primary Examiner*—Ali R. Salimi
(74) *Attorney, Agent, or Firm*—Elliot M. Olstein; Raymond J. Lillie

(57) ABSTRACT

The present invention provides immunogenic compositions and methods for inducing enhanced immune responses using an antigen and a combination of water soluble polymer and an amphiphilic compound.

11 Claims, No Drawings

IMMUNOADJUVANTS

This application claims the benefit of provisional application Ser. No. 60/106,326, filed Oct. 30, 1998.

This application relates to the field of polymers for biomedical applications, and in particular describes polymers in combination with amphiphilic compounds that are useful as immunoadjuvants.

BACKGROUND

A wide variety of antigens stimulate the production of antibodies in animals and confer protection against subsequent infection. However, some antigens are unable to stimulate an effective immune response.

The immunogenicity of a relatively weak antigen is often enhanced by the simultaneous administration of the antigen with an adjuvant, a substance that is not immunogenic when administered alone, but will induce a state of mucosal and/or systemic immunity when combined with the antigen. Unfortunately, many immunoadjuvants, such as Freund's Complete Adjuvant, are toxic and are therefore only useful for animal research purposes, not human vaccinations.

Ionically cross-linkable water soluble polymers, poly[di(carboxylatophenoxy)phosphazene]s (PCPPs) have been developed (Allcock, H. R. and S. Swan, *Macromolecules*, 22:75–79 (1989)). In the soluble state, PCPP has been demonstrated to have adjuvant activity (U.S. Pat. No. 5,494,673) and has enhanced the immunogenicity of various antigens (Payne, L. G. et al., *Vaccine*, 16:92–98(1998)). Generally, the addition of PCPP to antigen preparations has enhanced functional hemagglutination inhibition (HAI) antibody response and has enhanced IgM, IgG, and IgG1 ELISA antibody titers over the levels elicited by vaccine alone. PCPP as an adjuvant has been demonstrated to be as efficient as or to outperform complete Freund's adjuvant. The immunogenicity of antigens as diverse as tetanus toxoid, hepatitis B surface antigen, *Hemophilus influenzae* type b polyribosribotolphosphate, herpes simplex virus type 2 glycoprotein D and HIV env has been dramatically enhanced in the presence of soluble PCPP (Payne, L. G. et al., *Modulation of the Immune Response to Vaccine Antigens*, Lars Haaheim, ed, Geneva (1997); Lu, Y. et al., *J. AIDS Human Retrovirol.*, 12:99–106 (1996)).

SUMMARY OF THE INVENTION

The present invention provides a composition and method for inducing an effective immune response against an antigen, comprising an antigen and an adjuvant composition that includes (i) at least one water soluble polymer and (ii) at least one amphiphilic compound.

In a preferred embodiment, the water soluble polymer is a polyelectrolyte. The at least one water soluble polymer may or may not function as an adjuvant in the absence of the amphiphilic compound.

In a preferred embodiment, the at least one polymer has adjuvant properties in the absence of an amphiphilic compound.

The use of a combination of a water soluble polymer and an amphiphilic compound provides an improved adjuvant in that the combination provides an unexpected improvement over the use of either component in the absence of the other component.

For example, the use of such a combination can increase the humoral response to an antigen as compared to the use of either component alone.

In addition, the combination can provide a cytotoxic T lymphocyte (CTL) response to an antigen that is not present when using the antigen alone or the antigen with one of the two components of the composition of the invention in the absence of the other component and/or in the case where the antigen does generate a CTL response, the combination of the invention can improve such CTL response.

Although not bound to any particular theory or mechanism of action, it is believed that the unexpected beneficial immune response generated by the combination of the present invention may be due to a modification of the polymer component by the amphiphilic compound.

In another aspect the invention provides a method of inducing or enhancing an immunoprotective response to an immunological challenge in a host which comprises administering to said host an antigen and an adjuvant composition that includes (i) at least one water soluble polymer and (ii) at least one amphiphilic compound.

DETAILED DESCRIPTION OF THE INVENTION

The polymer portion of the adjuvant composition of the present invention is a water soluble polymer. The term water soluble means that the polymer is at least partially soluble in water (typically to an extent of at least 0.001% by weight), an aqueous buffered salt solution or aqueous alcohol solution. The polymer is preferably biodegradable and exhibits minimal toxicity when administered to animals including humans. The term polymer as used herein includes both homopolymers and copolymers.

Preferred natural water soluble polymers include alginate, gelatin, pectin, and collagen. Preferred synthetic water soluble polymers include poly(acrylamide), poly(methacrylamide), poly(vinyl acetate), poly(N-vinyl pyrrolidone), poly(hydroxyethylmethacrylate). poly(ethylene glycol), polyvinylamines, poly(vinylpyridine), poly(vinyl alcohols)and polyphosphazene.

In a preferred embodiment, the at least one polymer is a polyelectrolyte. The polyelectrolyte may be a polymer with anionic and/or cationic pendant groups.

As representative examples of anionic monomer units that form an anionic polymer there may be mentioned acrylic acid, methacrylic acid, styrenesulfonic acid, vinyl sulfonic acid, styrene carboxylic acid, maleic acid, 2-acrylamido-2-methylpropanesulfonic acid, 4-methylacryloyloxyethyl trimellitate, L-glutamic acid, L-aspartic acid, metaphosphoric acid, a phosphazene with a pendant anionic group(s), e.g. di(carboxylatophenoxy)phosphazene, or a salt thereof.

As representative examples of monomeric units that form cationic polymers, there may be mentioned ethyleneimine, vinylamine, 4-vinylpyridine, N,N-dimethylaminoethylmethacrylate, dimethylvinylbenzylamine, L-lysine, L-arginine and salts thereof.

In a preferred embodiment, the polymer is a water soluble polyphosphazene polyelectrolyte. Phosphazene is biodegradable and exhibits minimal toxicity when administered to animals, such as humans. Polyphosphazenes are polymers with backbones consisting of alternating phosphorus and nitrogen, separated by alternating single and double bonds. See U.S. Pat. No. 5,494,673 for representative examples of polyphosphazenes suitable for use in the present invention.

The other component of the adjuvant composition of the invention is an amphiphilic compound. The amphiphilic compound may or may not function as an adjuvant in the absence of the water soluble polymer.

The term amphiphilic compound as known in the art means that the compound includes both a hydrophobic portion and a hydrophilic portion.

Amphiphilic compounds suitable for producing the adjuvant of the present invention include dimyristoyl phosphatidylcholine, dimethyldioctadecylammonium bromide, N,N-dioctadecyl-N',N'-bis(2-hydroxyethyl) propanediamine, N-(2-Deoxy-2-L-leucylamino-β-D-glucopyranosyl)-N-octadecydodecanoylamide hydroacetate, dimyristoyl phosphatidylglycerol, N-acetylglucosaminyl-N-acetylmuramyl-L-Ala-D-isoGlu-L-Ala-glycerol dipalmitate, sorbitan trioleate, deoxycholic acid sodium salt, dicetyl phosphate, mono-palmitoyl-rac-glycerol, N-acetylglucosaminyl-N-acetylmuramyl-L-Ala-D-isoGlu-L-Ala-dipalmitoxy propylamide, octadecyl tyrosine hydrochloride, D-murapalmitine, 3-O-desacyl-4'-monophosphoryl lipid A, mannide oleate, 1a,25-dihydroxyvitamin $D_3$, phosphatidic acid, phosphatidylethanolamine, phosphatidylcholine, phosphatidylserine, phosphatidylinositol, sphingosine (D-4-sphingenine, ceramides, sphingomyelin, galactosylceramide, $GM_2$(ganglioside), salts of fatty acids including oleic acid, palmitic acid, capric acid, lauric acid, myristic acid, stearic acid, arachidic acid, behenic acid, lignoceric acid, cerotic acid, linoleic acid, linolenic acid, arachidonic acid, and the like.

In one aspect, the adjuvant can be prepared by mixing the water soluble polymer and the amphiphilic compound at room temperature. Antigen is then added to the adjuvant combination. Alternatively, the antigen is first mixed with one of the adjuvant components, and then the second adjuvant component is added. Preferably the immunogenic composition of the present invention is prepared by either mixing or conjugating the water soluble polymer with the antigen prior to administration. The water soluble polymer/antigen combination is then combined with the amphiphilic compound to form the immunogenic composition.

In accordance with the invention the adjuvant composition when combined with an antigen may be employed to produce a protective immune response in an animal (a human or non-human animal).

In accordance with another aspect the adjuvant composition in combination with an antigen may be employed to treat an animal (human or non-human).

The polymer can also be used to encapsulate the antigen and amphiphilic compound, for example, using the method of U.S. Pat. No. 5,149,543 to Cohen, et al., the teachings of which are incorporated herein, or by spray drying a solution of polymer, antigen and amphiphilic compound. Alternatively, microspheres containing the antigen and adjuvant can be prepared by simply mixing the components in an aqueous solution, and then coagulating the polymer together with the substance by mechanical forces to form a microparticle. See e.g. Andrianov, et al. U.S. Pat. No. 5,529,777. The microparticle can be stabilized, if necessary or desired, using electrolytes, pH changes, organic solvents, heat or frost to form polymer matrices encapsulating biological material. See U.S. Pat. No. 5,529,777. In one embodiment, the microspheres are generated by atomization of the water soluble polymer/amphiphilic compound antigen solution. Alternatively, the immunogenic composition can also be prepared by first forming water soluble polymer microspheres and the antigen solution and amphiphilic compound solution can be adsorbed or absorbed to the formed microsphere surface. This embodiment is especially advantageous when administration is through mucosal delivery.

The antigen is employed in an amount effective to produce the immune response required for treating and/or protecting against a disease.

The antigen used in the present invention can be derived from a cell, bacteria, or virus particle, or portion thereof. As defined herein, antigen may be a protein, peptide, polysaccharide, glycoprotein, glycolipid, nucleic acid, or combination thereof, which elicits an immunogenic response in an animal, for example, a mammal, bird, or fish. As defined herein, the immunogenic response can be humoral or cell mediated. In the event the material to which the immunogenic response is to be directed is poorly antigenic, it may be conjugated to a carrier such as albumin or to a hapten, using standard covalent binding techniques, for example, with one of the several commercially available reagent kits.

Examples of preferred antigens include viral proteins such as influenza proteins, human immunodeficiency virus (HIV) proteins, and hepatitis B proteins; and bacterial proteins and lipopolysaccharides such as gram negative bacterial cell walls and Neisseria gonorrhea proteins.

The polymer and the amphiphilic compound are employed in the composition in an amount to enhance the immunoprotective response of the antigen in producing a humoral and/or CTL response. In general, the amount of antigen and adjuvant present in the composition is such that the antigen generally does not exceed 5% by weight and in most cases does not exceed 2% by weight, based on antigen and adjuvant components.

In the adjuvant component, the polymer may be present in an amount of 1 molar up to 99 molar percent, and in general in an amount of at least 50 molar percent based on polymer and amphiphilic compounds.

The composition may further comprise one or more of a pharmaceutically acceptable carrier, diluent or extender such as are well known in the art.

The immunogenic composition can be administered as a vaccine by any method known to those skilled in the art that elicits an immune response, including parenterally, orally, or by transmembrane or transmucosal administration. Preferably, the vaccine is administered parenterally (intravenously, intramuscularly, subcutaneously, intraperitoneally, etc.), and preferably subcutaneously. Non-limiting examples of routes of delivery to mucosal surfaces are intranasal (or generally, the nasal associated lymphoid tissue), respiratory, vaginal, and rectal.

The dosage is determined by the antigen loading and by standard techniques for determining dosage and schedules for administration for each antigen, based on titer of antibody elicited by the polymer-amphiphilic compound antigen administration, as demonstrated herein.

The water soluble polymer-amphiphilic compound adjuvants will be further understood by reference to the following non-limiting example.

EXAMPLE

Materials

Antigen was derived from influenza virus strain X-31 (PR8 reassorted with Naichi/68 H3N2) (Spafas, Storrs, Conn.); was treated with detergent (Tween-20) and extracted with ether to produce "split antigen". Specifically, 34 mls (34 mg) of X-31 influenza and 85 microliters of Tween 80 were combined and allowed to nutate at room temperature for 30 minutes. 34 mls of ether was added and the mixture was allowed to nutate at room temperature for 30 minutes. The mixture was centrifuged for 15 minutes at 1500 rpm.

The top ether phase was removed and the sample was left uncovered until residual ether evaporated.

Poly[di(carboxylatophenoxy)-phosphazene] (PCPP) solution was prepared by dissolving 4 mg PCPP in 1 ml phosphate-buffered saline (PBS) pH 7.4 at 55° C. with agitation. The solution was sterilized with a 0.2 μm syringe filter (Gelman).

MPL is an acid hydrosylate of the lipopolysaccharide (LPS) of *Salmonella minnesota* R595, produced by the removal of a phosphate group from the reducing end of the lipid A moiety, converting toxic diphosphoryl lipid A into nontoxic monophosphoryl lipid A. Monophosphoryl lipid A (MPL) has also been utilized as an adjuvant. (Ulrich and Myers, *Vaccine Design: The Subunit and Adjuvant Approach* pp.495–524, Powell and Newman, eds. Plenum Press, New York, 1995). MPL incorporated into liposomes enhanced the specific CTL response to ovalbumin. Zhou and Huang, *Vaccine* 11(11) 1139–1144 (1993).

2 mgs of monophosphoryl Lipid A from *S. minnesota* R595 (MPL) (Ribi ImmunoChem Research, Inc. Hamilton, Mont.) powder was solubilized in 2 mls of $dH_2O$/chloroform-methanol solution (6 microliters of chloroform:methanol 4:1 (v/v) in 3 mls $dH_2O$) by alternating swirling in a 56° C. water bath and sonicating in an ultrasonic water bath two times.

Split X-31 in PBS: 1 μg (total protein) of split X-31 per dose was mixed by vortexing with PBS pH 7.4.

Split X-31 in PCPP: 1 μg (total protein) of split X-31 per dose was mixed by vortexing with PBS pH 7.4. PCPP solution was then added to a concentration of 100 μg/dose and mixed by vortexing.

Split X-31 in MPL: 1 μg (total protein) of X-31 per dose was mixed by vortexing with PBS pH 7.4. MPL solution was then added to a concentration of 50 μg/dose and mixed by vortexing.

Split X-31 in PCPP/MPL: 1 μg (total protein) of X-31 per dose was mixed by vortexing with PBS pH 7.4. PCPP solution was then added to a concentration of 100 μg/dose and mixed by vortexing. MPL solution was then added to a concentration of 50 μg/dose and mixed by vortexing.

Immunizations

Female 6–8 week old BALB/c mice were randomized into groups of 5. Mice were immunized subcutaneously in the loose skin over the neck with 0.2 ml of formulation by means of a 25 gauge needle. Blood samples were collected from the retro-orbital sinus of $CO_2$ anesthetized mice.

Assays

Antigen specific antibodies in mouse serum were determined by ELISA in 96-well microtiter plates coated with purified X-31 from allantoic fluid (Spafas) in sodium carbonate buffer, pH 9.6. Plates were washed four times with 0.5% Tween 20/PBS (Sigma, St. Louis, Mo.) and then coated with 2.5% bovine serum albumin/PBS (BSA/PBS) to blocking non-specific binding. Plates were washed four times with 0.5% Tween 20/PBS. Two-fold serial dilutions of sera in 1% BSA/PBS were added to the wells and the plate was incubated 1 hour at 37° C. Positive (anti-X31 positive mouse sera) and negative controls (normal mouse sera) were included on each plate. Unbound serum was washed and horseradish peroxidase-labelled goat anti-mouse IgG (Sigma) was added and incubated at 37° C. for 1 hour. Unbound conjugate was washed away and serum antibody was detected by adding 0.4 mg/ml solution of O-phenylenediamine dihydrochloride (OPD) (Sigma, St. Louis, Mo.) in 0.05 M phosphate-citrate phosphate buffer pH 5.0. The reaction was stopped after 30 minutes by the addition of 2M $H_2SO_4$ and the absorbances were read at 490 nm. The endpoint titers were defined as the reciprocal of the highest sample dilution producing a signal two-fold greater than that of the negative control at the same dilution. The IgG isotypes of the ELISA-reactive influenza-specific antibodies were determined as above using horseradish peroxidase-labelled goat anti-mouse $IgG_1$, $IgG_2$ and $IgG_{2b}$ (Boehringer Mannheim). Serum antibody was detected using OPD after an incubation time of 5 minutes. Antibody titers were expressed as geometric mean titers (GMT). The results are shown in Table 1.

The results indicate that 1 μg of influenza in 100 μg/50 μg PCPP/MPL induced a dramatically higher anti-influenza response than 1 μg of influenza in either PCPP or MPL alone. PCPP or MPL alone did not induce immune responses significantly higher than the PBS control formulation.

The ability of the PCPP/monophosphoryl lipase A solution to induce functional antibodies was assayed in a hemagglutination inhibition assay (HAI). Heat-inactivated mouse serum was incubated for 30 minutes with 10% chicken red blood cells (RBCs) (Spafas) to remove non-specific inhibitors. Two-fold dilutions of sera were added to a 96 well microtiter plate and 8 HA units of live X-31 virus suspension in an equal volume were added to each well and incubated at room temperature for 30 minutes. Positive (anti-X31 positive mouse sera) and negative controls (normal mouse sera) were included on each plate. A 0.5% suspension of chicken RBCs was added to each well and incubated at room temperature for 60 minutes. The HAI titers were expressed as the reciprocal of the highest dilution that completely inhibited hemagglutination of erythrocytes. Antibody titers were expressed as geometric mean titers (GMT). The results are shown in Table 1.

Once again, the PCPP monophosphoryl lipase A formulation induced much higher antibody activities in the hemagglutination assays whereas there was little or no activity detectable in the assay in formulations containing PCPP or MPL alone.

In a mouse potency test, an antigen dose that induces HAI antibody titers >40 units is predictive of protection in a human. Thus, 1 μg of total influenza antigen in 0.1% PCPP monophosphoryl lipase A was able to induce protective levels of antibody that were not achieved with 1 μg of antigen without adjuvant or with either PCPP or MPL alone.

The antibody isotypes engendered in this response were also assayed. Although the PCPP monophosphoryl lipase A formulated influenza antigen induced a response in all IgG subclasses tested, significant IgG1 response was detected. The level of response of HAI and IgG2a was dramatically increased over the lack of or limited response to flu without adjuvant or with either PCPP or MPL alone.

The results show that mice that received split antigen with either PCP or MPL alone had little or no detectable HAI or IgG2a titers, yet when the antigen was formulated with PCPP and MPL, together they elicited very high HAI and IgG2a responses.

TABLE 1

| Formulation | HAI | IgG | IgG1 | IgG2a | IgG2b |
| --- | --- | --- | --- | --- | --- |
| Flu/PBS | <20 | 147 | 294 | <64 | <64 |
| Flu/PCPP | <20 | 6208 | 6208 | <64 | 256 |
| Flu/MPL | <20 | 2048 | 891 | 84 | 256 |
| Flu/PCPP + MPL | 184 | 602249 | 228210 | 21619 | 32768 |

Modifications and variations of the present invention, polymer adjuvants and methods of synthesis and use in vaccine compositions, will be obvious to those skilled in the art from the foregoing detailed description. Such modifications and variations are intended to come within the scope of the claims.

What is claimed is:

1. A composition for inducing an immunogenic response in an animal comprising an antigen, at least one water soluble polymer and at least one amphiphilic compound.

2. The composition of claim 1 wherein the water soluble polymer is a polyelectrolyte.

3. The composition of claim 1 wherein the polyelectrolyte is a polyphosphazene.

4. The composition of claim 1 wherein the amphiphilic compound is selected from the group consisting of phospholipids, glycolipids, relatively long chain alkyl esters, fatty acid esters fatty amines and and monophosphoryl lipid A.

5. The composition of claim 1, wherein the antigen is an influenza virus strain X-31 protein.

6. A method for producing an immune response in an animal, comprising:
administering to said animal the composition of claim 1.

7. The method of claim 6 wherein the water soluble polyelectrolyte is a polyphosphazene.

8. The method of claim 6 wherein the amphiphilic compound is selected from the group consisting of phospholipids, glycolipids, relatively long chain alkyl esters, fatty acid esters fatty amines and and monophosphoryl lipid A.

9. The method of claim 7, wherein the polyphosphazene comprises poly(di(carboxylatophenoxy)phosphazene).

10. The method of claim 9 wherein the polyphosphazene is in the form of microspheres.

11. The method of claim 8 wherein the monophosphoryl Lipid A is from *S. minnesota* R595.

* * * * *